(12) United States Patent
Sun et al.

(10) Patent No.: US 8,067,481 B2
(45) Date of Patent: Nov. 29, 2011

(54) LOW SHRINKAGE DENTAL MATERIAL AND METHOD

(75) Inventors: Benjamin Jiemin Sun, York, PA (US); Andrew Murray Lichkus, York, PA (US)

(73) Assignee: Dentsply International, Inc., York, PA (US)

( * ) Notice: Subject to any disclaimer, the term of this patent is extended or adjusted under 35 U.S.C. 154(b) by 0 days.

(21) Appl. No.: 12/231,641

(22) Filed: Sep. 4, 2008

(65) Prior Publication Data

US 2010/0286435 A1   Nov. 11, 2010

(51) Int. Cl.
- *A61K 6/08* (2006.01)
- *C08G 65/14* (2006.01)
- *C08G 59/04* (2006.01)
- *A61C 5/00* (2006.01)

(52) U.S. Cl. ............ 523/115; 523/120; 433/228.1; 528/92; 528/103.5

(58) Field of Classification Search ............ 523/115, 523/120; 433/228.1; 528/92, 103.5
See application file for complete search history.

(56) References Cited

U.S. PATENT DOCUMENTS

| | | | | |
|---|---|---|---|---|
| 3,661,828 A | * | 5/1972 | Fellers et al. | 525/109 |
| 3,694,407 A | * | 9/1972 | Krikorian | 528/98 |
| 3,746,686 A | * | 7/1973 | Marshall et al. | 528/114 |
| 3,781,380 A | * | 12/1973 | Labana et al. | 525/208 |
| 3,817,946 A | * | 6/1974 | Ree | 526/273 |
| 4,421,897 A | * | 12/1983 | Gutekunst et al. | 525/119 |
| 4,452,847 A | * | 6/1984 | Siemon | 442/149 |
| 5,357,008 A | * | 10/1994 | Tsai et al. | 525/526 |
| 5,492,976 A | * | 2/1996 | Shalati et al. | 525/285 |
| 5,994,475 A | * | 11/1999 | Roth et al. | 525/326.7 |
| 6,057,383 A | * | 5/2000 | Volkel et al. | 523/116 |
| 6,541,541 B2 | * | 4/2003 | Masamune et al. | 523/217 |
| 6,592,369 B2 | * | 7/2003 | Sun et al. | 433/167 |
| 6,799,969 B2 | * | 10/2004 | Sun et al. | 433/167 |
| 7,682,691 B2 | * | 3/2010 | Akaho et al. | 428/339 |
| 2008/0021166 A1 | * | 1/2008 | Tong et al. | 525/241 |
| 2009/0278285 A1 | * | 11/2009 | Sun et al. | 264/406 |

FOREIGN PATENT DOCUMENTS

| | | | |
|---|---|---|---|
| JP | 401057269 A | * | 3/1989 |
| WO | WO 03/076544 | * | 9/2003 |

* cited by examiner

*Primary Examiner* — Tae H Yoon

(74) *Attorney, Agent, or Firm* — Douglas J. Hura; David A. Zdurne; Leana Levin

(57) ABSTRACT

The invention provides a low polymerization shrinkage dental composition and a polymerizable dental material selected from the group consisting of wax-like dental material that undergoes ring open polymerization. The dental composition is useful as restorative material and for making artificial teeth, dentures, restoratives, crowns and bridges of high strength dental polymeric material.

13 Claims, No Drawings

LOW SHRINKAGE DENTAL MATERIAL AND METHOD

RELATED APPLICATIONS

This application claims the benefit of U.S. patent application Ser. No. 11/271,304 filed on Nov. 10, 2005 which claims the benefit of U.S. Provisional Application Ser. No. 60/627,199 filed on Nov. 12, 2004.

TECHNICAL FIELD

The invention relates to wax-like polymerizable materials. This wax-like polymerizable dental material is quickly and easily reshaped. The shaped wax-like polymerizable dental material is cured to form dental products, such as crowns, bridges, dentures, and other restoration devices and appliances.

BACKGROUND OF THE INVENTION

Volkel et at in U.S. Pat. No. 6,057,383 (and Canadian Patent Application 2207351), assigned to Ivoclar, disclose wax-like polymerizable material for making entire dental products. The prior art does not disclose a wax-like polymerizable material for forming dentures or other high toughness products.

DETAILED DESCRIPTION OF THE INVENTION

The invention provides wax-like polymerizable dental material and restorative paste wax polymerizable dental material. Wax-like polymerizable dental materials of this invention have low polymerization shrinkage. The polymerization of wax-like material of this invention involves ring opening polymerization as well as volume expansion from phase change to reduce the polymerization shrinkage. Previous epoxy-based resins do not have wax-like handling characteristics and not involve volume expansion from phase change. Wax-like polymerizable dental material is flowable at and above 40° C., and becomes dimensionally stable at and below 23° C., within 5 minutes. Paste wax material is flowable at and above 50° C., and becomes dimensionally stable at and below 37° C., within 5 minutes. These polymerizable dental materials may include filler particles, fiber and/or rubber-modified high molecular weight resin. These polymerizable dental materials are useful in tooth restorative fillings, adhesives, cements, denture base materials, orthodontic materials and sealants, for repair of defects in natural dentition, and to form crowns, bridges, full dentures, partial dentures, denture liners, custom trays, artificial teeth, repairs for natural teeth, veneers, denture repairs, denture reline, night guards, splints, retainers, orthodontic components, burn out parts, provisional dental devices, inlays, onlays, orthodontic appliances, oral orthopedic appliances, temporary dentures, temporary partial dentures, maxillofacial prostheses, obturators, and occular prostheses, etc.

Polymerizable dental material in accordance with the invention may include from 0 to about 95 percent by weight filler particles. In a preferred embodiment of the invention polymerizable dental materials include from about 5 to about 90 percent by weight filler. More preferably, these polymerizable dental materials include from about 20 to about 85 percent by weight filler. Most preferably, these polymerizable dental materials include from about 40 to about 80 percent by weight filler.

The filler particles have a range of particles sizes from 0.001 micrometers to 10 micrometers. The filler particles preferably include organic and/or inorganic particles, and preferably reduce polymerization shrinkage, improve wear resistance and modify the mechanical and physical properties. Preferred fillers are glasses formed from or including, barium, calcium, strontium, lanthanum, tantalum, and/or tungsten silicates and aluminates and/or aluminosilicates, silica, quartz, ceramics, nanoparticles. Preferably the filler particles have a range of particle sizes of from 0.001 micrometers to 10 micrometers.

The polymerizable dental materials of the invention are quickly and easily reshaped, for example by warming, and shaping it while warm and then allowing it to cool to body (37° C.) or room temperature (23° C.). The cooled polymerizable dental materials may be worked for example by packing, molding, shaping, and/or carving. The worked polymerizable dental materials are cured.

The polymerizable dental materials of the invention preferably include from about 1 to about 100 percent by weight of a crystalline resin and from about 0 to 99 percent by weight of an amorphous component. When heated, the polymerizable dental materials soften and are more flowable and less crystalline.

Wax-like polymerizable dental material and restorative paste wax polymerizable dental material of the invention may include pigments, initiators, catalysts, stabilizers, plasticizers and fibers. Preferred stabilizers are butylated hydroxytoluene (BHT) and the methyl ether of hydroquinone (MEHQ).

Polymerizable dental materials of the invention may include one or more initiating systems to cause them to harden promptly. Light curable wax-like polymerizable dental composites preferably include at least a light sensitizer, for example camphorquinone, 4-octyloxy-phenyl-phenyl iodonium hexafluoroantimonate (OPPI), 2,4,6-trimethylbenzoyl-diphenylphosphine oxide, or methyl benzoin which causes polymerization to be initiated upon exposure to activating wavelengths of light; and/or a reducing compound, for example tertiary amine.

A room temperature or heat activating catalyst system is preferably included in polymerizable dental materials of the invention. For example a peroxide capable of producing free radicals when activated by a reducing agent at room temperature or by heating. Preferred peroxides include benzyl peroxide and lauroyl peroxide.

Compounds, which are readily partially crystallizable and useful in wax-like polymerizable dental material of a preferred embodiment of the invention, include epoxy, epoxy methacrylate (or acrylate), methacrylate (or acrylate) compounds or their combinations. Epoxy compounds polymerizes by ring-opening polymerization shrinks less due to the increase in excluded free-volume associated with the ring-opening process in addition to the volume expansion from the phase conversion.

Polymerizable dental materials of the invention are preferably rapidly partially recrystallizable. Rapid recrystallizability provides the densification of the polymeric products and a combination of flowability and dimensional stability, depending on its temperature prior to polymerization. When polymerized, the crystallized phase melts effective resulting in volume expansion, which offsets polymerization shrinkage. The combination of volume expansion from phase change and ring-opening process ensures the low polymerization shrinkage or even polymerization expansion. Thus, the polymeric products are low shrinkage and low stress restorations and devices. "Crystallinity" as used herein refers to regularity and order within a material resulting in a heat of fusion of at least 1.0 J/g at and below 50° C. Heat of Fusion as used herein refers to enthalpy of fusion as determined by ASTM 793-95. Percent crystallinity is determined by measuring the heat of fusion using differential scanning calorimetry according to ASTM test method E 793-95.

A preferred embodiment of the invention provides a dental polymeric material formed by light curing wax-like polymerizable dental material and restorative paste wax polymerizable dental material. "Flexural strength, and flexural modulus" as used herein refers to results of testing according to ASTM D790 (1997).

"Wax-like" as used herein refers to material which is flowable (fluid) at and above 40° C., and becomes dimensionally stable (solidifies: i.e. is non-fluid) at least at and below 23° C., within 5 minutes. Thus, wax-like material is flowable when it is at and above 40° C., and becomes dimensionally stable when it is at and below 23° C. Flowable wax-like material having a temperature from 100° C. to 40° C., becomes dimensionally stable within 5 minutes by cooling by exposure to an ambient temperature between 37° C. and 0° C. Flowable wax-like composite paste having a temperature from 100° C. to 40° C., becomes dimensionally stable within (in order of increasing preference) 4, 2, 1 or 0.5 minutes by cooling by exposure to an ambient temperature between 23° C. and 0° C.

"Restorative Paste Wax" as used herein refers to material which is flowable (fluid) at and above 50° C., and becomes dimensionally stable (solidifies: i.e. is non-fluid) at least at and below 37° C., within 5 minutes. Thus, restorative paste wax is flowable when it is at and above 50° C., and becomes dimensionally stable when it is at and below 37° C. Flowable restorative paste wax having a temperature from 100° C. to 50° C., becomes dimensionally stable within 5 minutes by cooling by exposure to an ambient temperature between 37° C. and 0° C. Flowable restorative paste wax having a temperature from 100° C. to 50° C., becomes dimensionally stable within (in order of increasing preference) 4, 2, 1 or 0.5 minutes by cooling by exposure to an ambient temperature between 37° C. and 0° C. Restorative paste wax may be flowable throughout all of the temperature range from 49° C. to 38° C.; it may be dimensionally stable throughout all of the temperature range from 49° C. to 38° C.; or it may be flowable in part and dimensionally stable in part of the temperature range from 49° C. to 38° C.

Dimensional stability is determined by testing according to ADA (American Dental Association) consistency test specification 19, paragraph 4.3.4, JAVA Vol. 94, April, 1977, pages 734-737 at 23° C. Fluids change shape uniformly in response to external force imposed on them (see *Hawley's Condensed Chemical Dictionary* 1997, page 507, at fluid).

In order of increasing preference polymerization shrinkage of wax-like polymerizable dental material and restorative paste wax polymerizable dental material of the invention is less than 3 percent by volume, less than 2 percent by volume, less than 1.5 percent by volume, less than 1 percent by volume, less than 0.5 percent by volume. In order of increasing preference polymerization shrinkage of restorative paste wax polymerizable dental material of the invention is less than 3 percent by volume, less than 2 percent by volume, less than 1.5 percent by volume, less than 1 percent by volume, less than 0.5 percent by volume.

A preferred embodiment of the invention provides a prepared cavity in a tooth in a patient's mouth, which is then filled by injection from a syringe of dental filling material in accordance with the invention. Preferably the syringe is heated to from 42° C. to 60° C., and has a readily disconnected and interchangeable nozzle with a generally cylindrical internal passage having an internal diameter of from about 0.5 mm to about 5.0 mm. The dental filling material cools and solidifies rapidly in the prepared cavity in the tooth to about 37° C. Thus, a syringe is provided having an inner chamber and a nozzle. The nozzle has a nozzle passage in fluid flow communication with the inner chamber. The inner chamber encloses wax-like polymerizable dental material or restorative paste wax polymerizable dental material. Then the polymerizable dental material is polymerized.

A preferred embodiment of the invention provides a prepared cavity in a tooth in a patient's mouth, which is then filled by positioning in the prepared cavity a composition including at least 40 percent by weight filler and a polymerizable dental material selected from the group consisting of wax-like polymerizable dental material and restorative paste wax polymerizable dental material. Then the polymerizable dental material is light cured to form dental polymeric material with a shrinkage during polymerization of less than 2 percent by volume. The polymerizable dental material includes a portion of crystals, which melt during polymerization. The crystals are believed to be crystals of oligomer and/or crystals of monomer. The volume of the liquid formed by melting the crystals is greater than the volume of the crystals. This expansion reduces the shrinkage of the polymerizable dental material caused by polymerization. In addition, the wax-like polymerizable materials of this invention showed low polymerization shrinkage due to the ring opening process involved. This invention provides low polymerization shrinkage materials with and without fillers. Furthermore, low polymerization shrinkage materials offer low stress restorations and low stressed cured dental devices.

Moreover, the compositions of this invention provide a system with two types of initiators to initiate rapid free radical polymerization and relatively slower cationic polymerization. The incorporation of cationic polymerization slows down the complete polymerization conversion process, so as to reduce polymerization stress and more effective introduction of stress reduction by volume expansion from melting phase change and ring opening process.

In the following examples, unless otherwise indicated, all parts and percentages are by weight; Lucirin TPO refers to 2,4,6-trimethylbenzoyldiphenylphosphine oxide and liquid Lucirin refers to ethyl-2,4,6-trimethylbenzoylphenylphosphinate made by BASF.

Example 1A

Preparation of Epoxy Oligomer

Epoxy oligomer was prepared by mixing of 0.2 gram of 2-methylimidazole and 41.25 grams of bis(3,4-epoxy-6-methylcyclohexylmethyl)adipate, and 26.0 grams of 1,10 decanediol. Then the mixture is stirred under nitrogen for 8 hours at temperatures between 120 to 150° C. After the reaction, resin is collected as yellow liquid and cooled down to room temperature to form gel-like waxy solid.

Example 1B

Preparation of Epoxy Oligomer

Epoxy oligomer I was prepared by mixing of 0.12 gram of 2-methylimidazole and 29.3 grams of bisphenol A propoxylate diglycidyl ether, 16.2 grams of 1,10-decanediol in a three-neck flask. Then the mixture is stirred under nitrogen for 8 hours at temperatures from 100 to 150° C. After the reaction, light yellow resin is collected and cooled down to room temperature to form soft wax-like resin.

Example 2A

Preparation of Monomer

A reaction flask was charged with 700 grams of 1,6-diisocyanatohexane and heated to about 70° C. under a positive nitrogen pressure. To this reactor were added 1027 grams of 2-hydroxyethyl methacrylate, 0.75 gram of catalyst dibutyltin dilaurate and 4.5 grams of butylated hydroxy toluene (BHT). The addition was slow and under dry nitrogen flow over a period of two hours. The temperature of the reaction mixture was maintained between 70° C. and 90° C. for another two hours and followed by the addition of 8.5 grams of purified water. One hour later, the reaction product was discharged as clear liquid into plastic containers and cooled to form a white solid and stored in a dry atmosphere.

Example 2B

Preparation of Monomer

A reaction flask was charged with 43.8 grams of 1,12-diisocyanatododecane and heated to about 80° C. under a positive nitrogen pressure. To this reactor were added 45.0 grams of 2-hydroxyethyl methacrylate, 0.075 gram of catalyst dibutyltin dilaurate and 0.19 grams of butylated hydroxy toluene (BHT). The addition was slow and under dry nitrogen flow over a period of one hour. The temperature of the reaction mixture was maintained between 80° C. and 90° C. for another one hour and followed by the addition of 0.15 gram of purified water. One hour later, the reaction product was discharged as clear liquid into plastic container and cooled to form a white solid and stored in a dry atmosphere.

Example 3

Preparation of Epoxy Oligomer

Epoxy oligomer I was prepared by mixing of 0.12 gram of 2-methylimidazole and 29.3 grams of bisphenol A propoxylate diglycidyl ether, 16.2 grams of 1,10-decanediol in a three-neck flask. Then the mixture is stirred under nitrogen for 8 hours at temperatures from 100 to 150° C. After the reaction, light yellow resin is collected and cooled down to room temperature to form soft wax-like resin.

Example 4A

Preparation of Polymerizable Wax-Like Material

A wax-like polymerizable dental material was prepared by stirring at 85° C. a liquid mixture of 2.6 grams of oligomer made the procedure of Example 1B, 1.8 grams of bisphenol A propoxylate diglycidyl ether, 0.063 gram 4-octyloxy-phenyl iodonium hexafluoroantimonate (OPPI), 0.063 gram of camphorquinone (CQ), 0.004 gram of red acetate fibers, 0.014 gram of pigment concentrates.

Example 5

Preparation of Polymerizable Denture Setup Material

A wax-like polymerizable dental material was prepared by stirring at 85° C. a liquid mixture of 68.25 grams of bisphenol A propoxylate diglycidyl ether, 30.0 grams of 1,10-decanediol, 1.0 gram 4-octyloxy-phenyl iodonium hexafluoroantimonate (OPPI), 0.35 gram of 2,4,6-trimethylbenzoyldiphenylphosphine oxide, (Lucirin TPO made by BASF), 0.1 gram of red acetate fibers, 0.3 gram of pigment concentrates.

Example 6

Preparation of Polymerizable Denture Contour Material

A wax-like polymerizable dental material was prepared by stirring at 85° C. a liquid mixture of 48.25 grams of bisphenol A propoxylate diglycidyl ether, 50.0 grams of polycaprolactone diol (average Mn, ~2000), 1.0 gram 4-octyloxy-phenyl iodonium hexafluoroantimonate (OPPI), 0.35 gram of 2,4,6-trimethylbenzoyldiphenylphosphine oxide, (Lucirin TPO made by BASF), 0.1 gram of red acetate fibers, 0.3 gram of pigment concentrates.

Examples 7A Through 7D

Table 1 shows the components of the compositions of Examples 7A through 7D. The compositions of Examples 7A through 7D were prepared by mixing the components shown in Table 1 at 90° C.

TABLE 1

| Components | 7A | 7B | 7C | 7D |
|---|---|---|---|---|
| Camphorquinone (CQ) | 0.17 | 0.17 | 0.15 | 0.2 |
| 4-Octyloxy-phenyl-phenyl iodonium hexafluoroantimonate (OPPI) | 0.33 | 0.33 | 0.3 | 0.4 |
| Bisphenol A propoxylate diglycidyl ether | 23.5 | | | |
| 3,4-Epoxycyclohexyl methyl 3,4-epoxycyclohexanecarboxylate | | 19.5 | 16.55 | |
| Bis(3,4-epoxycyclohexylmethyl)adipate | | | | 29.4 |
| 1,10-decanediol | 6 | | 3 | 5 |
| Polycaprolactone (Mn ~2000) | | | 5 | 5 |
| 2,5-Dimethyl-2,5-hexandiol | | 5 | | |
| Silanated barium aluminoflurosilicate glass (BAFG)* (EG) | 14 | 15 | 15 | 11 |
| Silanated barium aluminoflurosilicate glass (BAFG)** (U/F) | 56 | 60 | 60 | 49 |

*particles having an average particle size of from about 1 to about 10 micrometers.
**particles having an average particle size of from about 0.1 to about 1 micrometers.

Example 8

Filling Material

A cavity in a natural tooth in a patient's mouth is prepared by drilling, and then brushing onto the drilled cavity about 0.02 ml of PRIME & BOND NT dual cure bonding agent, sold by Dentsply International Inc. Then the bonding agent is light cured by impinging light thereon for 30 seconds from a Spectrum 800 light curing unit sold by Dentsply International Inc. The prepared cavity is then filled with 0.2 g of the product of Example 7A, which is then light cured by impinging light thereon for 30 seconds from a Spectrum 800 light curing unit sold by Dentsply International Inc.

Example 9A

Crown

A crown is formed by molding about 0.5 g of the product of Example 7B. A surface of natural tooth in a patient's mouth is prepared for the crown by cutting and polishing, and then brushing onto the polished surface about 0.05 ml of PRIME & BOND NT dual cure bonding agent, sold by Dentsply International Inc. Then the crown is set onto the prepared surface. The crown and the bonding agent are then light cured by impinging light thereon for 60 seconds from a Spectrum 800 light curing unit sold by Dentsply International Inc.

Example 9B

Veneer

A veneer is formed by molding about 0.3 g of the product of Example 7C. A surface of natural tooth in a patient's mouth is prepared for the veneer by cutting and polishing, and then brushing onto the polished surface 0.03 ml of PRIME & BOND NT dual cure bonding agent, sold by Dentsply International Inc. Then the veneer is set onto the prepared surface. The veneer and the bonding agent are then light cured by impinging light thereon for 60 seconds from a Spectrum 800 light curing unit sold by Dentsply International Inc.

Example 9C

Filling Material

A natural dentition in a patient's mouth in need of restoration is selected. A cavity in the tooth is prepared by drilling, and then brushing onto the drilled cavity 0.02 ml of PRIME & BOND NT dual cure bonding agent, sold by Dentsply International Inc. Then the bonding agent is light cured by impinging light thereon for 30 seconds from a Spectrum 800 light curing unit sold by Dentsply International Inc. The prepared cavity is then filled by injection into the cavity of 0.2 g of the product of Example 7D from a syringe having a nozzle with an internal passage diameter of about 2 mm. The syringe is warmed to 50° C., and has a chamber filled with the dental filling material product of Example 7D. The dental filling material cools to 37° C. and solidifies rapidly with excellent shape stability. The cooled filling material is carved and sculptured to conform to the contour and shape of the tooth. The cooled dental filling material is then light cured by impinging light thereon for 30 seconds from a Spectrum 800 light curing unit sold by Dentsply International Inc.

Example 10

Green Tooth

A tooth is formed by molding 0.6 g of the product of Example 7C into the shape of a natural tooth.

Example 11

High Strength Tooth

The tooth formed in Example 10 is light cured by impinging light thereon for 10 minutes from an Eclipse light curing unit sold by Dentsply International Inc. A high strength polymeric artificial tooth is formed which has a polymerization shrinkage of less than 2 percent by volume.

It should be understood that while the present invention has been described in considerable detail with respect to certain specific embodiments thereof, it should not be considered limited to such embodiments but may be used in other ways without departure from the spirit of the invention and the scope of the appended claims.

What is claimed is:

1. A polymerizable dental material having improved resistance to shrinkage, comprising
   a crystallizable material that can be melted and which exhibits a volume expansion upon melting, said material is formed from an epoxy oligomer which can be initiated to undergo ring open polymerization; and
   a system having at least two initiators to initiate rapid free radical polymerization and relatively slower cationic polymerization.

2. A dental material as in claim 1, wherein said crystallizable material is flowable at temperatures above 40 degrees C. and which is dimensionally stable below 23 degrees C.

3. A dental material as in claim 1, wherein said crystallizable material is wax-like.

4. A dental material as in claim 1, wherein said epoxy oligomer is the reaction product of an imidazole and an adipate having epoxy functionality.

5. A dental material as in claim 4, wherein said imidazole is 2-methylimidazole.

6. A dental material as in claim 4, wherein said adipate is bis(3,4-epoxy-6-methylcyclohexylmethyl)adipate.

7. A dental material as in claim 4, wherein said reaction product is further obtained in the presence of a diol.

8. A dental material as in claim 7, wherein said diol is 1,10 decanediol.

9. A dental material as in claim 1, wherein said epoxy oligomer is the reaction product of an imidazole; an ether having epoxy functionality and a diol.

10. A dental material as in claim 9, wherein said imidazole is 2-methylimidazole.

11. A dental material as in claim 9, wherein said ether is bisphenol A propoxylate diglycidyl ether.

12. A dental material as in claim 9, wherein said diol is 1,10 decanediol.

13. A dental material as in claim 1, wherein said epoxy oligomer is the reaction product of an imidazole, bisphenol A propoxylate diglycidyl ether and a diol.

* * * * *